(12) United States Patent
Mathison

(10) Patent No.: US 9,889,047 B2
(45) Date of Patent: Feb. 13, 2018

(54) PROTECTIVE SHIELD FOR MALE GENITALIA

(71) Applicant: Richard Mathison, Hamilton (CA)

(72) Inventor: Richard Mathison, Hamilton (CA)

(*) Notice: Subject to any disclaimer, the term of this patent is extended or adjusted under 35 U.S.C. 154(b) by 753 days.

(21) Appl. No.: 14/469,357

(22) Filed: Aug. 26, 2014

(65) Prior Publication Data

US 2015/0053210 A1    Feb. 26, 2015

Related U.S. Application Data

(60) Provisional application No. 61/870,205, filed on Aug. 26, 2013.

(51) Int. Cl.
*A61F 13/47*   (2006.01)
*A61F 13/471*   (2006.01)
*A61F 13/15*   (2006.01)

(52) U.S. Cl.
CPC ........ *A61F 13/4704* (2013.01); *A61F 13/471* (2013.01); *A61F 2013/15146* (2013.01)

(58) Field of Classification Search
CPC ................ A61F 13/4704; A61F 13/471; A61F 2013/15146; A61H 19/00
See application file for complete search history.

(56) References Cited

U.S. PATENT DOCUMENTS

| | | | | |
|---|---|---|---|---|
| 1,052,765 A | * | 2/1913 | Strauss | A41B 9/02 |
| | | | | 602/67 |
| 4,195,630 A | * | 4/1980 | Connery | A41B 9/023 |
| | | | | 2/403 |
| 4,471,772 A | * | 9/1984 | Miller, Jr. | A41B 9/023 |
| | | | | 2/403 |
| 4,622,962 A | * | 11/1986 | Kauffman | A41B 9/023 |
| | | | | 602/70 |
| 5,074,853 A | | 12/1991 | Bryant | |
| 5,351,699 A | * | 10/1994 | Hammons | A61F 6/04 |
| | | | | 128/844 |
| 6,295,651 B1 | * | 10/2001 | Kang | A41B 9/02 |
| | | | | 2/400 |

FOREIGN PATENT DOCUMENTS

DE    20 2004 002 526 U1    7/2004

\* cited by examiner

*Primary Examiner* — Tarla Patel
(74) *Attorney, Agent, or Firm* — Muncy, Geissler, Olds & Lowe, P.C.

(57) ABSTRACT

The present disclosure relates to an incontinence device, more particularly a protective shield for male genitalia.

6 Claims, 6 Drawing Sheets

PROTECTIVE SHIELD FOR MALE GENITALIA

TECHNICAL FIELD

The present disclosure relates to incontinence devices, and more particularly a protective shield for male genitalia.

BACKGROUND

Incontinence is a difficult and embarrassing problem, and numerous devices for dealing with male incontinence are known. These range from conventional adult diapers to more specialized devices which wrap around a user's penis, such as those taught by German Patent Document No. 20 2004 002 526 U1 and U.S. Pat. No. 5,074,853. Conventional adult diapers can be less comfortable than a person's ordinary underwear, and must account for the possibility of shifting positions of the penis therewithin, which can cause the urethral opening to be positioned at different locations. While devices that wrap around the penis allow a user to wear his own underwear and can ensure that the urethral opening remains covered by absorbent material regardless of penis position, they can be cumbersome to remove for ordinary urination.

SUMMARY

A protective shield for male genitalia wraps around the user's penis and is secured to the user's underwear to form a pouch to receive the glans of the penis and absorb leaking urine. The protective shield is secured to the user's underwear in such a way that pulling the waistband of the underwear inferiorly away from the groin will expose the penis for urination.

A protective shield for male genitalia comprises a flexible substrate having an outer surface and a penis-facing surface opposite the outer surface. The protective shield has a penis-encircling portion for circumferentially encircling the shaft of a penis, a glans-receiving portion for receiving the glans of the penis and an underwear-engaging portion for securing to an inside front face of the user's underwear, with the underwear-engaging portion including at least one affixing element on the outer surface. When the protective shield is in a flattened condition, the glans-receiving portion is disposed between the underwear-engaging portion and the penis-encircling portion. In use, the penis-encircling portion is secured about the shaft of the penis so as to circumferentially encircle the shaft of the penis, the underwear-engaging portion is secured to the inside front face of the underwear by the at least one affixing element, and the protective shield is movable between a protective configuration and a urinating configuration. In the protective configuration, the protective shield is folded over on itself so that the penis-encircling portion faces the underwear-engaging portion and the glans-receiving portion forms a pouch that receives the glans of the penis, with the underwear-engaging portion disposed exteriorly of the penis-encircling portion. The protective shield is moved from the protective configuration to the urinating configuration by moving the inside front face of the underwear inferiorly away from the penis to release the glans of the penis from the pouch formed by the glans-receiving portion and expose the penis for urination while the shaft of the penis remains encircled by the penis-encircling portion.

Preferably, the glans-receiving portion has elasticized edges to assist in forming the pouch.

The present disclosure is also directed to a method of using a protective shield.

BRIEF DESCRIPTION OF THE DRAWINGS

These and other features will become more apparent from the following description in which reference is made to the appended drawings wherein.

DETAILED DESCRIPTION

Figure 1:
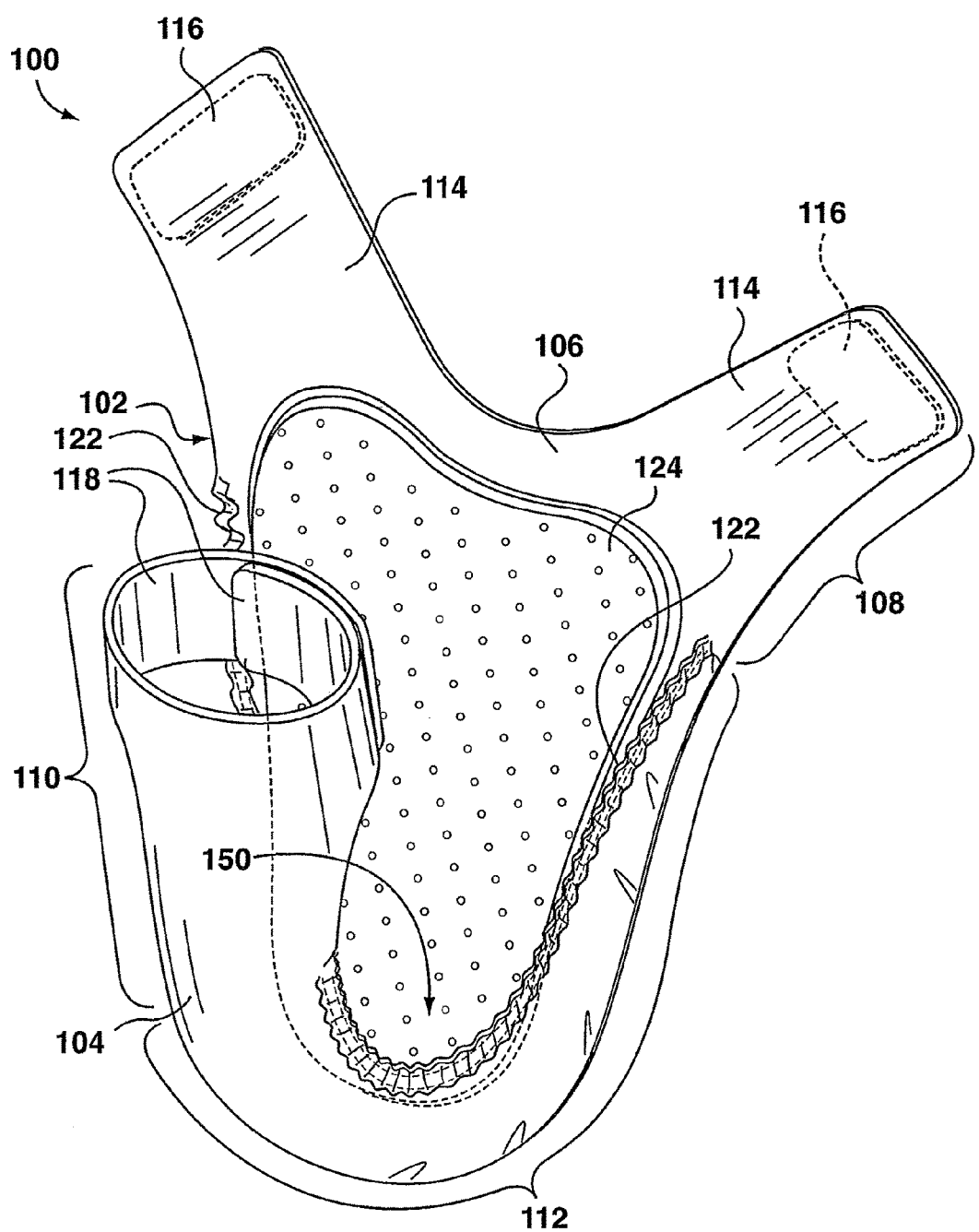
FIG. 1 shows a first exemplary embodiment of a protective shield for male genitalia, with the protective shield in a protective configuration.
Figure 4:
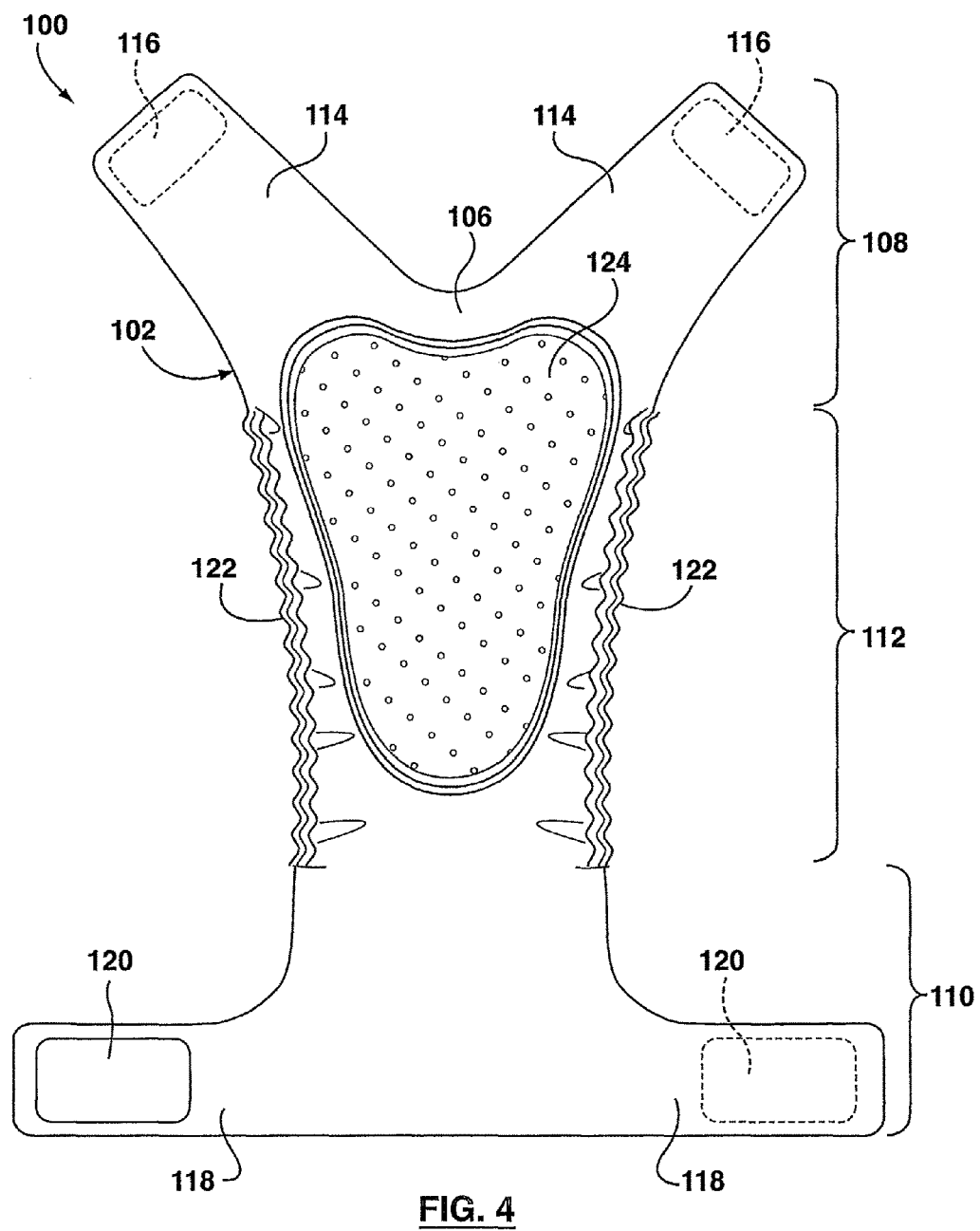
FIG. 4 shows the protective shield of FIG. 1 in a flattened configuration.

Reference is now made to FIGS. 1 and 4, in which a first exemplary embodiment of a protective shield for male genitalia is indicated generally by the reference numeral 100. FIG. 1 shows the protective shield 100 in a protective configuration it would assume when in use, and FIG. 4 shows the protective shield 100 in a flattened condition. The protective shield 100 comprises a flexible substrate 102 having an outer surface 104 and a penis-facing surface 106 opposite the outer surface 104. The flexible substrate 102 may be, for example, a single- or multi-layer cloth substrate, a single- or multi-layer plastic substrate, or a multi-layer composite substrate such as those used in conventional infant or adult diapers.

The flexible substrate 102 has an underwear-engaging portion 108 for securing to the inside front face of underwear, a penis-encircling portion 110 for circumferentially encircling the shaft of the user's penis, and a glans-receiving portion 112 for receiving the glans of the user's penis. When the protective shield 100 is in a flattened condition, as shown in FIG. 4, the glans-receiving portion 112 is disposed between the underwear-engaging portion 108 and the penis-encircling portion 110.

The underwear-engaging portion 108 includes at least one affixing element to enable the underwear-engaging portion 108 to be secured to the inside front face of underwear. In the embodiment shown in FIGS. 1 to 4 the underwear-engaging portion 108 comprises two opposed outwardly extending fixing arms 114 with the affixing elements taking the form of adhesive elements 116 disposed on the outer surface 104 of the underwear-engaging portion 108 at the ends of the fixing arms 114. The adhesive elements 116 are similar to those used in conventional diapers, and may include a peelably removable protective sheet to prevent premature adhesion. Other types of affixing elements may be used instead of adhesive elements, including without limitation hooks, pins, clips or the hook portions of hook-and-loop fasteners to engage the fabric of the underwear as the loops (or corresponding loop portions on underwear specifically designed or modified for use with such a protective shield).

In the exemplary embodiment shown in FIGS. 1 to 4, the penis-encircling portion 110 comprises a pair of opposed straps 118 which can be secured to one another in overlapping relation by way of complementary hook-and-loop fastener elements 120 (FIG. 4). Alternatively, one or more adhesive elements may be used in place of the hook-and-loop fastener elements. The glans-receiving portion 112 has elasticized edges 122, and includes an absorbent pad 124. The absorbent pad 124 may be of any suitable construction; many suitable arrangements for absorbent pads are known in the art and will not be detailed here. Where the protective shield 100 is of a single-use, disposable type, the absorbent pad 124 may be relatively permanently secured to, or integral with, the flexible substrate 102. Where the protective shield 100 is intended for reuse, the absorbent pad 124 may be releasably secured to the flexible substrate 102, for example by adhesive, so that the absorbent pad 124 is of a single-use disposable type while the flexible substrate 102 is reused. In the further alternative, a reusable protective shield 100 may include a washable and reusable absorbent pad 124 that is relatively permanently affixed to a washable and reusable flexible substrate 102.

A method of using the protective shield 100 will now be described with reference to FIGS. 2 and 3. In particular, in use the protective shield 100 is movable between a protective configuration (FIG. 2) in which the protective shield 100 absorbs fluid which may leak from the urethral opening, and a urinating configuration (FIG. 3) enabling deliberate urination.

A user who is installing the exemplary protective shield 100 would secure the penis-encircling portion 110 about the shaft 140 of his penis 142 by fastening the opposed straps 118 to one another so that the opposed straps 118 circumferentially encircle the shaft 140 of the penis 142, and secure the underwear-engaging portion 108 to the inside of the front face 144 of the underwear 146 by adhering the adhesive elements 116 to the inside of the front face 144 of the underwear 146. These steps may be done in any order. For example, a user may secure the penis-encircling portion 110 about the shaft 140 of his penis 142 before putting on his underwear 146, or with his underwear below his hips. The user can then move his underwear 146 into the usual wearing position and then pull the waistband 148 outwardly to create room to adhere the adhesive elements 116 to the inside of the front face 144 of the underwear 146. Alternatively, before putting on his underwear 146, or with the underwear 146 below its usual wearing position, the user can adhere the adhesive elements 116 to the inside front face 144 of the underwear 146, and then move the underwear 146 to the usual wearing position and pull the waistband 148 outwardly to create room to fasten the opposed straps 118 to one another so that the opposed straps 118 circumferentially encircle the shaft 140 of the penis 142. In the further alternative, the user may fasten the opposed straps 118 to one another and adhere the adhesive elements 116 to the inside front face 144 of the underwear 146 with the underwear 146 in the usual wearing position.

Figure 2:
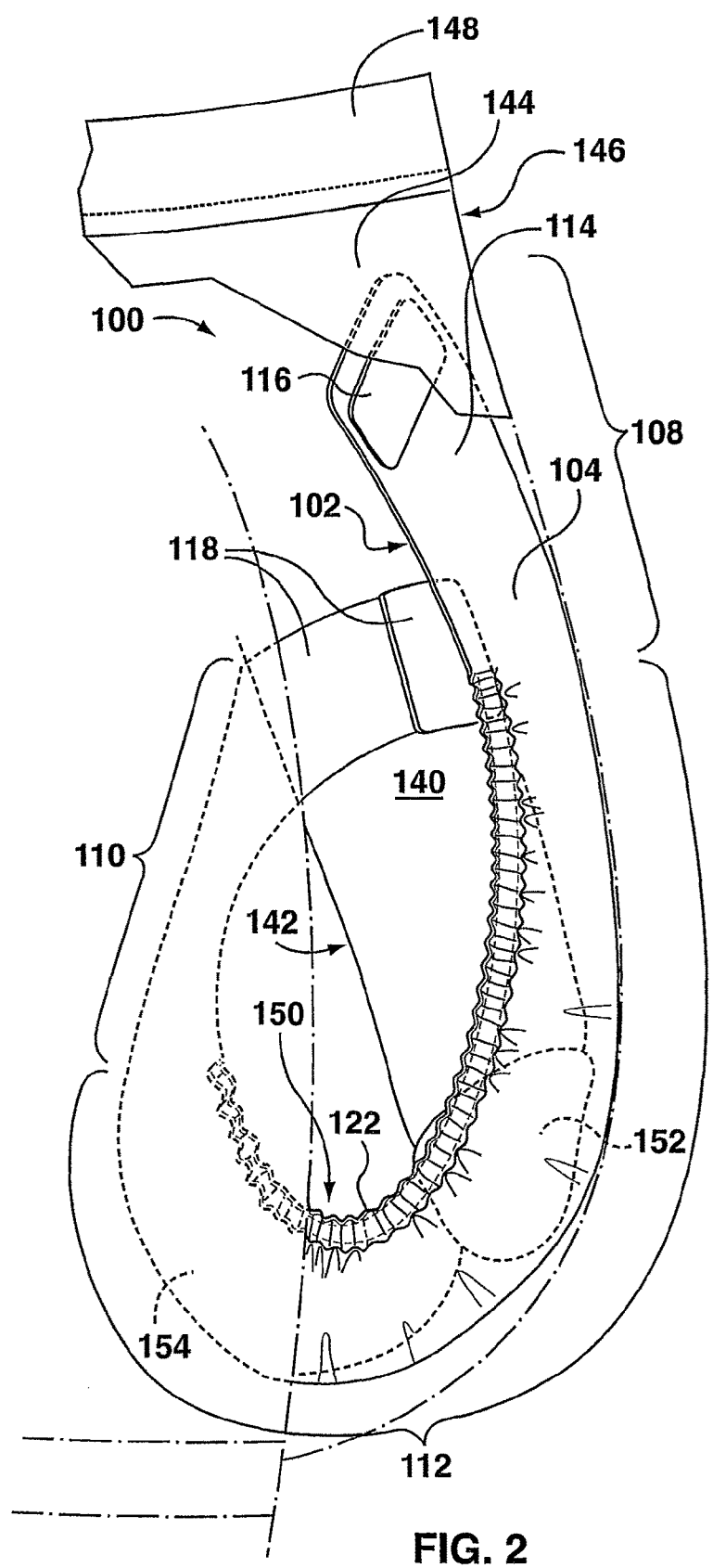
FIG. 2 shows the protective shield of FIG. 1 in use in a protective configuration.

Once the penis-encircling portion 110 is secured about the shaft 140 of the penis 142 and the adhesive elements 116 are adhered to the inside front face 144 of the underwear 146 with the underwear 146 in the usual wearing position, as shown in FIG. 2, the protective shield is in the protective configuration.

In the protective configuration, the protective shield 100 is folded over on itself so that the penis-encircling portion 110 faces the underwear-engaging portion 108 and the glans-receiving portion 112 forms a pouch 150 that receives the glans (head) 152 of the penis 142, with the elasticized edges 122 assisting in forming the pouch 150. With the glans 152 so received, urine leaking from the urethral opening will be received in the pouch 150 for absorption by the absorbent pad 124. In the protective configuration, the underwear-engaging portion 108 is disposed exteriorly of the penis-encircling portion 110. The scrotum 154, including the testes, is preferably placed inside the pouch 150 for comfort as shown in the drawings. Alternatively, although less preferably, the scrotum 154 may be positioned exteriorly of the penis-encircling portion, with the penis-encircling portion 110 disposed between the scrotum 154 and the penis 142. The choice of whether to place the scrotum 154 inside or outside of the penis-encircling portion 112 is a matter of which is more comfortable for the user.

Figure 3:
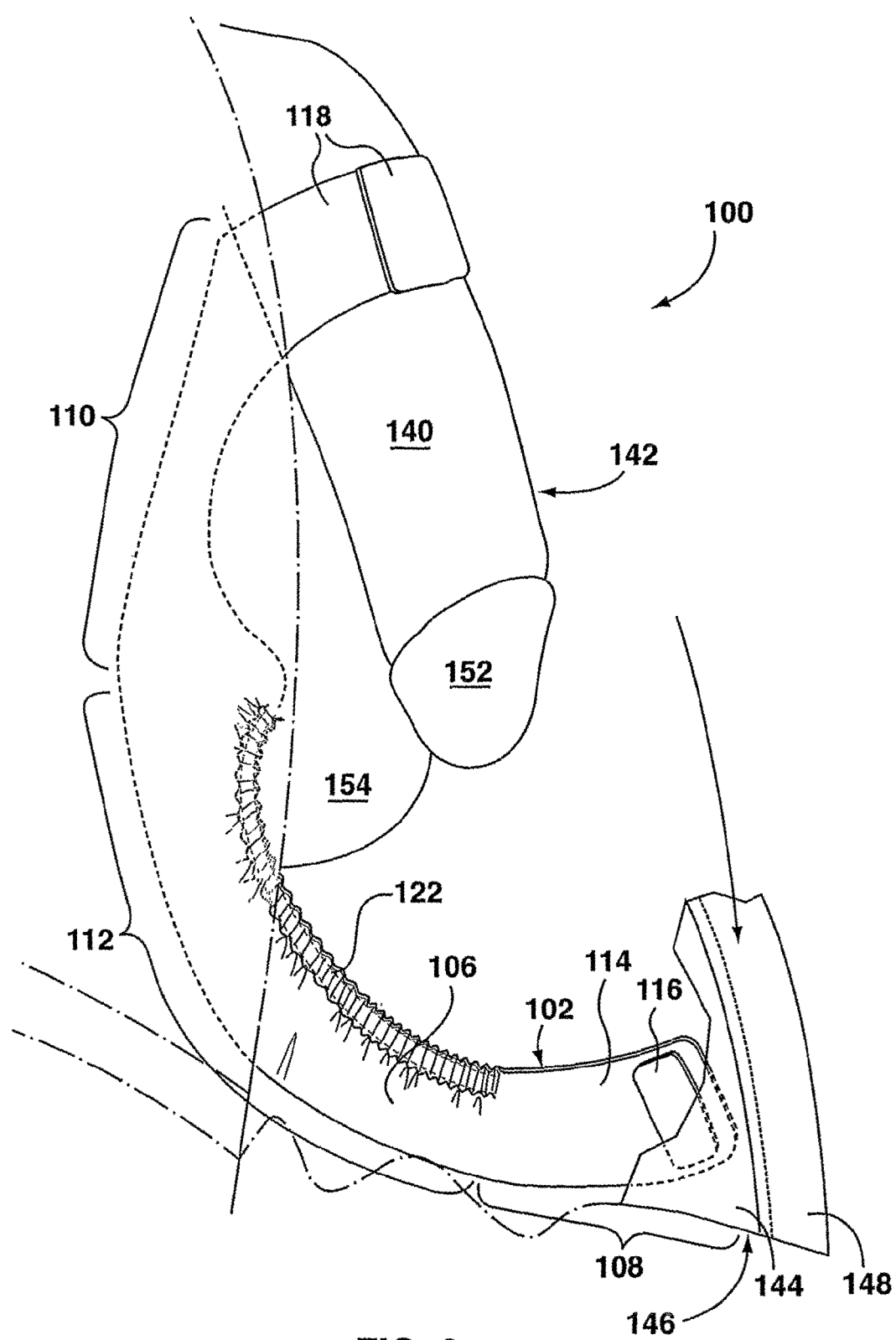
FIG. 3 shows the protective shield of FIG. 1 in use in a urination configuration.

The protective shield 100 is moved from the protective configuration shown in FIG. 2 to the urinating configuration shown in FIG. 3 by moving the inside front face 144 of the underwear 146 inferiorly away from the penis 142, for example by pulling the waistband 148 downwardly while standing. This releases the glans 152 of the penis 142 from the pouch 150 formed by the glans-receiving portion 112 and exposes the penis 142 for urination while the shaft 140 of the penis 142 remains encircled by the penis-encircling portion 110, as shown in FIG. 4. For example, the penis 142 could then be pulled through a pant fly (not shown) to urinate in a urinal (not shown).

Figure 5:
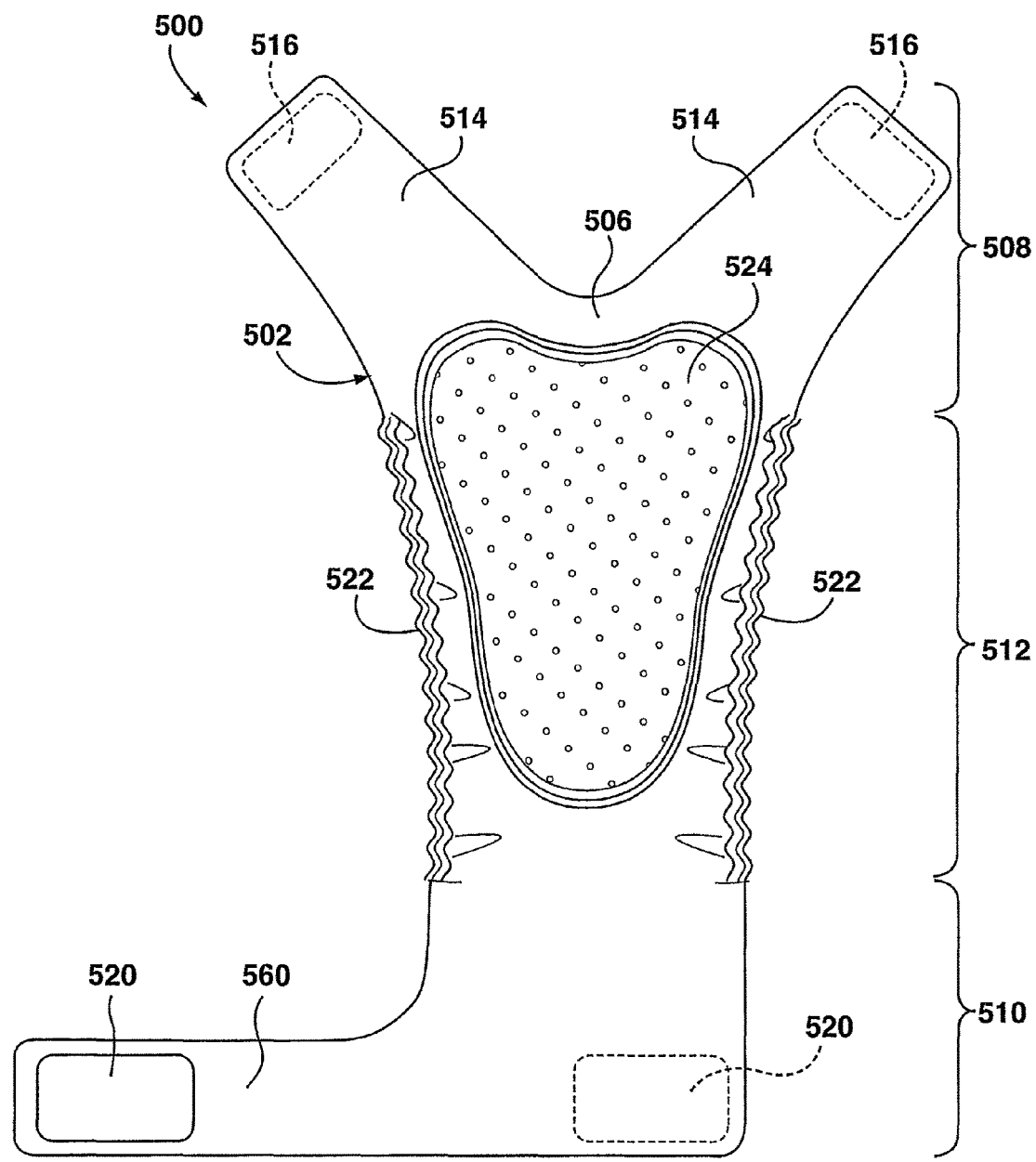
FIG. 5 shows a second exemplary embodiment of a protective shield for male genitalia, with the protective shield in a flattened configuration.
Figure 6:
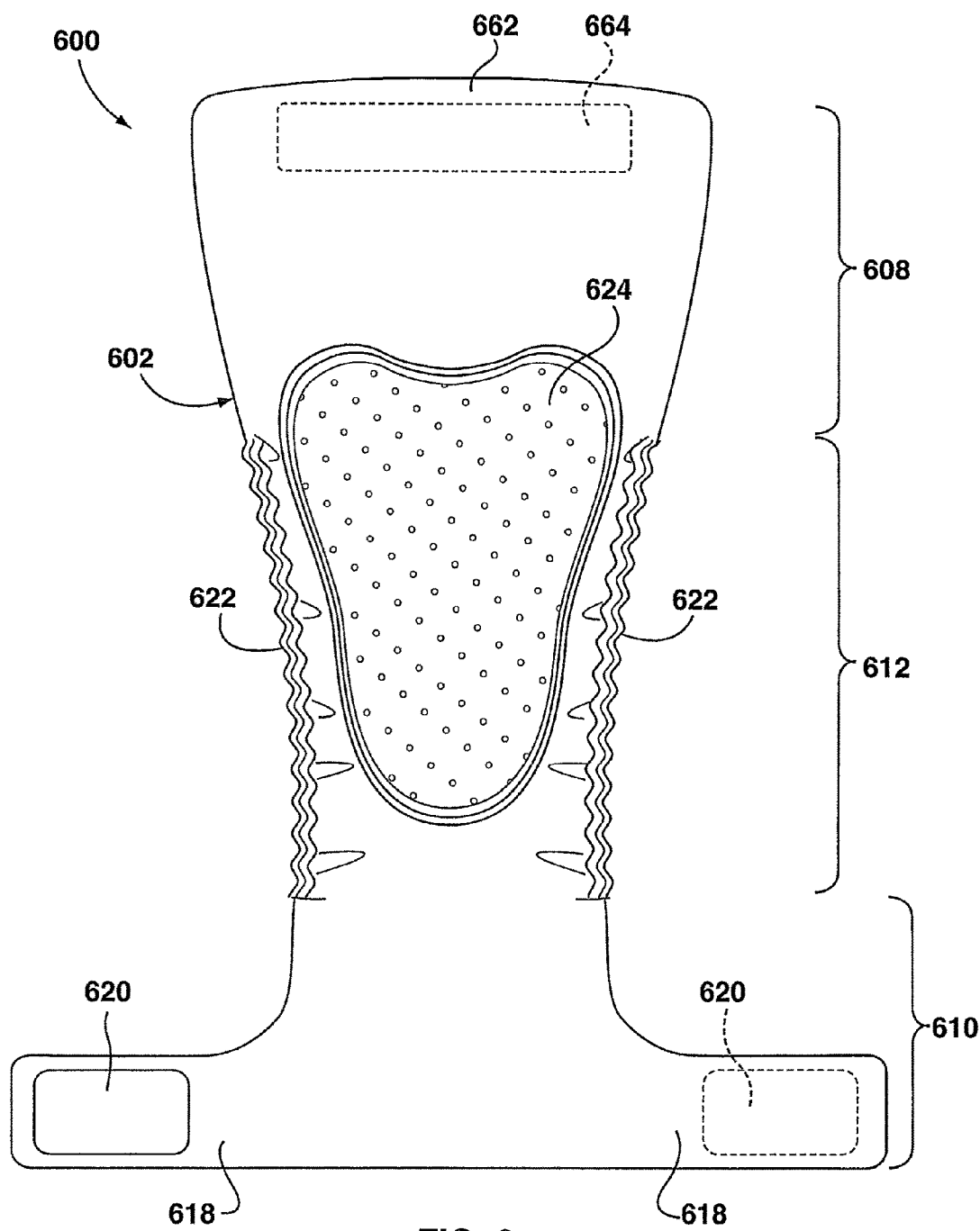
FIG. 6 shows a third exemplary embodiment of a protective shield for male genitalia, with the protective shield in a flattened configuration.

The protective shield 100 shown in FIGS. 1 to 4 is merely one exemplary embodiment. FIG. 5 shows a second embodiment of a protective shield 500. The protective shield 500 shown in FIG. 5 is similar to the protective shield 100 shown in FIG. 1, with corresponding reference numerals referring to corresponding features except with the prefix "5" instead of "1". Instead of a pair of opposed straps 118 (FIG. 1) which can be secured to one another in overlapping relation, the penis-encircling portion 510 comprises a single strap 560 for encircling the penis. FIG. 6 shows a third embodiment of a protective shield 300, which is also similar to the protective shield 100 shown in FIG. 1, with corresponding reference numerals referring to corresponding features except with the prefix "6" instead of "1". The protective shield 600 shown in FIG. 6 differs from the protective shield 100 shown in FIG. 1 in that instead of two opposed outwardly extending fixing arms, the underwear-engaging portion 608 comprises a single generally rectangular region 662 with a single elongate adhesive element adhesive element 664. Further variations are also possible.

Protective shields as described herein may be used with virtually any type of underwear, including boxers, briefs and even thongs.

Several embodiments have been described by way of example. It will be apparent to persons skilled in the art that a number of variations and modifications can be made without departing from the scope of the invention as defined in the claims.

What is claimed is:
1. A protective shield for male genitalia, comprising:
   a flexible substrate having an outer surface and a penis-facing surface opposite the outer surface, the flexible substrate having a first longitudinal end and a second longitudinal end opposite the first longitudinal end and having:
   an underwear-engaging portion at the first longitudinal end for securing to an inside front face of underwear, the underwear-engaging portion including at least one affixing element on the outer surface;

a penis-encircling portion at the second longitudinal end configured to circumferentially encircle a shaft of a penis; and a glans-receiving portion configured to receive a glans of the penis;

the glans-receiving portion being disposed between the underwear-engaging portion and the penis-encircling portion and between the first longitudinal end and the second longitudinal end;

the penis-encircling portion being configured to be secured about the shaft of the penis so as to circumferentially encircle the shaft of the penis and support the second longitudinal end; and the underwear-engaging portion being secured to the inside front face of the underwear by the at least one affixing element;

the protective shield being movable between a protective configuration and a urinating configuration:

in the protective configuration, the protective shield being folded over on itself so that the penis-encircling portion faces the underwear-engaging portion and the glans-receiving portion forms a pouch that is configured to receive the glans of the penis; and the underwear-engaging portion is disposed exteriorly of the penis-encircling portion; and the protective shield is moved from the protective configuration to the urinating configuration by moving the inside front face of the underwear inferiorly away from the penis to release the glans of the penis from the pouch formed by the glans-receiving portion and expose the penis for urination while the shaft of the penis remains encircled by the penis-encircling portion.

2. The protective shield of claim 1, wherein glans-receiving portion has elasticized edges to assist in forming the pouch.

3. The protective shield of claim 1, wherein the penis-encircling portion includes at least one elongated strap having a longitudinal direction perpendicular to the longitudinal direction of the flexible substrate.

4. The protective shield of claim 3, wherein the penis-encircling portion includes two straps with an affixing element.

5. The protective shield of claim 1, wherein the glans-receiving portion includes an absorbent pad.

6. The protective shield of claim 1, wherein the first longitudinal end has two branches in a Y-configuration.

* * * * *